(12) United States Patent
Cohen et al.

(10) Patent No.: US 6,172,195 B1
(45) Date of Patent: Jan. 9, 2001

(54) IKAP PROTEINS AND METHODS

(75) Inventors: Lucie Cohen; Patrick Baeuerle, both of South San Francisco, CA (US)

(73) Assignee: Tularik Inc., South San Francisco, CA (US)

( * ) Notice: Under 35 U.S.C. 154(b), the term of this patent shall be extended for 0 days.

(21) Appl. No.: 09/286,891

(22) Filed: Apr. 6, 1999

Related U.S. Application Data (62) Division of application No. 08/971,244, filed on Nov. 16, 1997, now Pat. No. 5,891,719.

(51) Int. Cl.$^7$ .................................................. C07K 1/00
(52) U.S. Cl. ........................ 530/350; 530/300; 530/351; 436/501
(58) Field of Search .................... 530/350, 351, 530/300; 536/23.5; 435/6, 69.1, 69.5, 252.3; 436/501

(56) References Cited

FOREIGN PATENT DOCUMENTS

WO 94/01548  1/1994 (WO).

OTHER PUBLICATIONS

Database GenBank, National Library of Medicine, Bethesda, Maryland USA, Accession No. H19711, Hillier et al., yn60b07.rl *Homo sapiens* cDNA clone 172789 5'. Jul. 03, 1995.

Database GenBank, National Library of Medicine, Bethesda, Maryland USA, Accession No. N31333, Hillier et al., yx54c03.rl *Homo sapiens* cDNA clone 265540 5'. Jan. 10, 1996.

Database GenBank, National Library of Medicine, Bethesda, Maryland USA, Accession No. H15327, Hillier et al., ym28d08.rl *Homo sapiens* cDNA clone 49526 5'. Jun. 27, 1995.

Database GenBank, National Library of Medicine, Bethesda, Maryland USA, Accession No. AA478901, Hilier et al., zv20c02.rl Soares NhHMPu S1 *Homo sapiens* cDNA clone 754178 5'. Aug. 08, 1997.

Database GenBank, National Library of Medicine, Bethesda, Maryland USA, Accession No. AA324126, Hillier et al., EST27019 Cerebellum II *Homo sapiens* cDNA 5' end. Apr. 20, 1997.

*Primary Examiner*—Elizabeth Kemmerer
*Assistant Examiner*—Michael Brannock
(74) *Attorney, Agent, or Firm*—Richard Aron Osman (57) ABSTRACT

The invention provides methods and compositions relating to IKAP proteins which regulate cellular signal transduction and transcriptional activation, and related nucleic acids. The polypeptides may be produced recombinantly from transformed host cells from the disclosed IKAP encoding nucleic acids or purified from human cells. The invention provides isolated IKAP hybridization probes and primers capable of specifically hybridizing with the disclosed IKAP genes, IKAP-specific binding agents such as specific antibodies, and methods of making and using the subject compositions in diagnosis, therapy and in the biopharmaceutical industry.

26 Claims, 1 Drawing Sheet

FIG. 1

IKAP PROTEINS AND METHODS

This is a divisional application of U.S. Ser. No. 08/971,244, filed Nov. 16, 1997, now U.S. Pat. No. 5,891,719, which is incorporated herein by reference.

FIELD OF THE INVENTION

The field of this invention is proteins involved in cell signal transduction.

BACKGROUND

Cytokines trigger changes in gene expression by modifying the activity of otherwise latent transcription factors (Hill and Treisman, 1995). Nuclear factor κB (NF-κB) is a 1prominent example of how such an external stimulus is converted into an active transcription factor (Verma et al., 1995). The NF-κB system is composed of homo- and heterodimers of members of the Rel family of related transcription factors that control the expression of numerous immune and inflammatory response genes as well as important viral genes (Lenardo and Baltimore, 1989; Baeuerle and Henkel, 1994). The activity of NF-κB transcription factors is regulated by their subcellular localization (Verma et al., 1995). In most cell types, NF-κB is present as a heterodimer comprising of a 50 kDa and a 65 kDa subunit. This heterodimer is sequestered in the cytoplasm in association with IκBα a member of the IκB family of inhibitory proteins (Finco and Baldwin, 1995; Thanos and Maniatis, 1995; Verma et al., 1995). IκBα masks the nuclear localization signal of NF-κB and thereby prevents NF-κB nuclear translocation. Conversion of NF-κB into an active transcription factor that translocates into the nucleus and binds to cognate DNA sequences requires the phosphorylation and subsequent ubiquitin-dependent degradation of IκBα in the 26s proteasome. Signal-induced phosphorylation of IκBα occurs at serines 32 and 36. Mutation of one or both of these serines renders IκBα resistant to ubiquitination and proteolytic degradation (Chen et al., 1995); DiDonato, 1996 #370, Roff, 1996 #397.

The pleiotropic cytokines tumor necrosis factor (TNF) and interleukin-1 (IL-1) are among the physiological inducers of IκB phosphorylation and subsequent NF-κB activation (Osborn et al., 1989; Beg et al., 1993). Although TNF and IL-1 initiate signaling cascades leading to NF-κB activation via distinct families of cell-surface receptors (Smith et al., 1994; Dinarello, 1996), both pathways utilize members of the TNF receptor-associated factor (TRAF) family of adaptor proteins as signal transducers (Rothe et al., 1995; Hsu et al., 1996; Cao et al., 1996b). TRAF proteins were originally found to associate directly with the cytoplasmic domains of several members of the TNF receptor family including the 75 kDa TNF receptor (TNFR2), CD40, CD30, and the lymphotoxin-β receptor (Rothe et al., 1994; Hu et al., 1994; Cheng et al., 1995; Mosialos et al., 1995; Song and Donner, 1995; Sato et al., 1995; Lee et al., 1996; Gedrich et al., 1996; Ansieau et al., 1996). In addition, TRAF proteins are recruited indirectly to the 55 kDa TNF receptor (TNFR1) by the adaptor protein TRADD (Hsu et al., 1996). Activation of NF-κB by TNF requires TRAF2 (Rothe et al., 1995; Hsu et al., 1996). TRAF5 has also been implicated in NF-κB activation by members of the TNF receptor family (Nakano et al., 1996); Ishida, 1996 #240. In contrast, TRAF6 participates in NF-κB activation by IL-1 (Cao et al., 1996b). Upon IL-1 treatment, TRAF6 associates with IRAK, a serine-threonine kinase that binds to the IL-1 receptor complex (Cao et al., 1996a); Huang, 1997 #400.

The NF-κB-inducing kinase (NIK) is a member of the MAP kinase kinase kinase (MAP3K) family that was identified as a TRAF2-interacting protein (Malinin et al., 1997). NIK activates NF-κB when overexpressed, and kinase-inactive mutants of NIK comprising its TRAF2-interacting C-terminal domain ($NIK_{(624-947)}$) or lacking two crucial lysine residues in its kinase domain ($NIK_{(KK429-430AA)}$) behave as dominant-negative inhibitors that suppress TNF-, IL-1-, and TRAF2-induced NF-κB activation (Malinin et al., 1997). Recently, NIK was found to associate with additional members of the TRAF family, including TRAF5 and TRAF6. Catalytically inactive mutants of NIK also inhibited TRAF5- and TRAF6-induced NF-κB activation, thus providing a unifying concept for NIK as a common mediator in the NF-κB signaling cascades triggered by TNF and IL-1 downstream of TRAFs. Recently two NIK-interacting protein designated characterized as novel human kinase IκB Kinases, IKK-α and IKKβ have been reported (Woronicz et al., 1997; Mercurio et al. 1997; Maniatis, 1997). Catalytically inactive mutants of IKK suppress NF-κB activation induced by TNF and IL-1 stimulation as well as by TRAF and NIK overexpression; transiently expressed IKK associates with endogenous IκBα complex; and IKK phosphorylates IκBα on serines 32 and 36.

Relevant Literature

Ansieau, S., et al. (1996). Proc. Natl. Acad. Sci. USA 93, 14053–14058.

Baeuerle, P. A., and Henkel, T. (1994). Annu. Rev. Immunol. 12, 141–179.

Beg, A. A., et al. (1993). Mol. Cell. Biol. 13, 3301–3310.

Cao, Z., Henzel, W. J., and Gao, X. (1996a). Science 271, 1128–1131.

Cao, Z., et al. (1996b). Nature 383, 443–446.

Chen, Z., et al. (1995). Genes Dev. 9, 1586–1597.

Cheng, G., et al. (1995). Science 267, 1494–1498.

Connelly, M. A., and Marcu, K. B. (1995). Cell. Mol. Biol. Res. 41, 537–549.

Dinarello, C. A. (1996). Biologic basis for interleukin-1 in disease. Blood 87, 2095–2147.

Fields, S., and Song, O.-k. (1989). Nature 340, 245–246.

Finco, T. S., and Baldwin, A. S. (1995). Immunity 3, 263–272.

Gedrich, R. W., et al. (1996). J. Biol. Chem. 271, 12852–12858.

Hill, C. S., and Treisman, R. (1995). Cell 80, 199–211.

Hsu, H., Shu, H.-B., Pan, M.-P., and Goeddel, D. V. (1996). Cell 84, 299–308.

Hu, H. M., et al. (1994). J. Biol. Chem. 269, 30069–30072.

Lee, S. Y., et al. (1996). Proc. Natl. Acad. Sci. USA 93, 9699–9703.

Lenardo, M., and Baltimore, D. (1989). Cell 58, 227–229.

Malinin, N. L., et al. (1997). Nature 385, 540–544.

Maniatis (1997) Science 278, 818.

Mercurio et al. (1997) Science 278, 860.

Mock et al. (1995). Genomics 27, 348–351.

Mosialos, G., et al. (1995). Cell 80, 389–399.

Nakano, H., et al. (1996). J. Biol. Chem. 271, 14661–14664.

Osborn, L., et al. (1989). Proc. Natl. Acad. Sci. USA 86, 2336–2340.

Rothe, M., Sarma, V., Dixit, V. M., and Goeddel, D. V. (1995). Science 269, 1424–1427.

Rothe, M., Wong, S. C., Henzel, W. J., and Goeddel, D. V. (1994). Cell 78, 681–692.

Sato, T., Irie, S., and Reed, J. C. (1995). FEBS Lett. 358, 113–118.

Schindler, U., and Baichwal, V. R. (1994). Mol. Cell. Biol. 14, 5820–5831.

Smith, C. A., Farrah, T., and Goodwin, R. G. (1994). Cell 76, 959–962.
Song, H. Y., and Donner, D. B. (1995). Biochem. J. 809, 825–829.
Thanos, D., and Maniatis, T. (1995). Cell 80, 529–532.
Woronicz et al., (1997) Science 278, 866.
Verma, I. M., et al. (1995). Genes Dev. 9, 2723–2735.

SUMMARY OF THE INVENTION

The invention provides methods and compositions relating to isolated IKAP polypeptides, related nucleic acids, polypeptide domains thereof having IKAP-specific structure and activity and modulators of IKAP function, particularly NIK binding activity. IKAP polypeptides can regulate NFκB activation and hence provide important regulators of cell function. The polypeptides may be produced recombinantly from transformed host cells from the subject IKAP polypeptide encoding nucleic acids or purified from mammalian cells. The invention provides isolated IKAP hybridization probes and primers capable of specifically hybridizing with the disclosed IKAP gene, IKAP-specific binding agents such as specific antibodies, and methods of making and using the subject compositions in diagnosis (e.g. genetic hybridization screens for IKAP transcripts), therapy (e.g. IKAP inhibitors to inhibit TNF signal transduction) and in the biopharmaceutical industry (e.g. as immunogens, reagents for isolating other transcriptional regulators, reagents for screening chemical libraries for lead pharmacological agents, etc.).

DETAILED DESCRIPTION OF THE INVENTION

Figure 1:
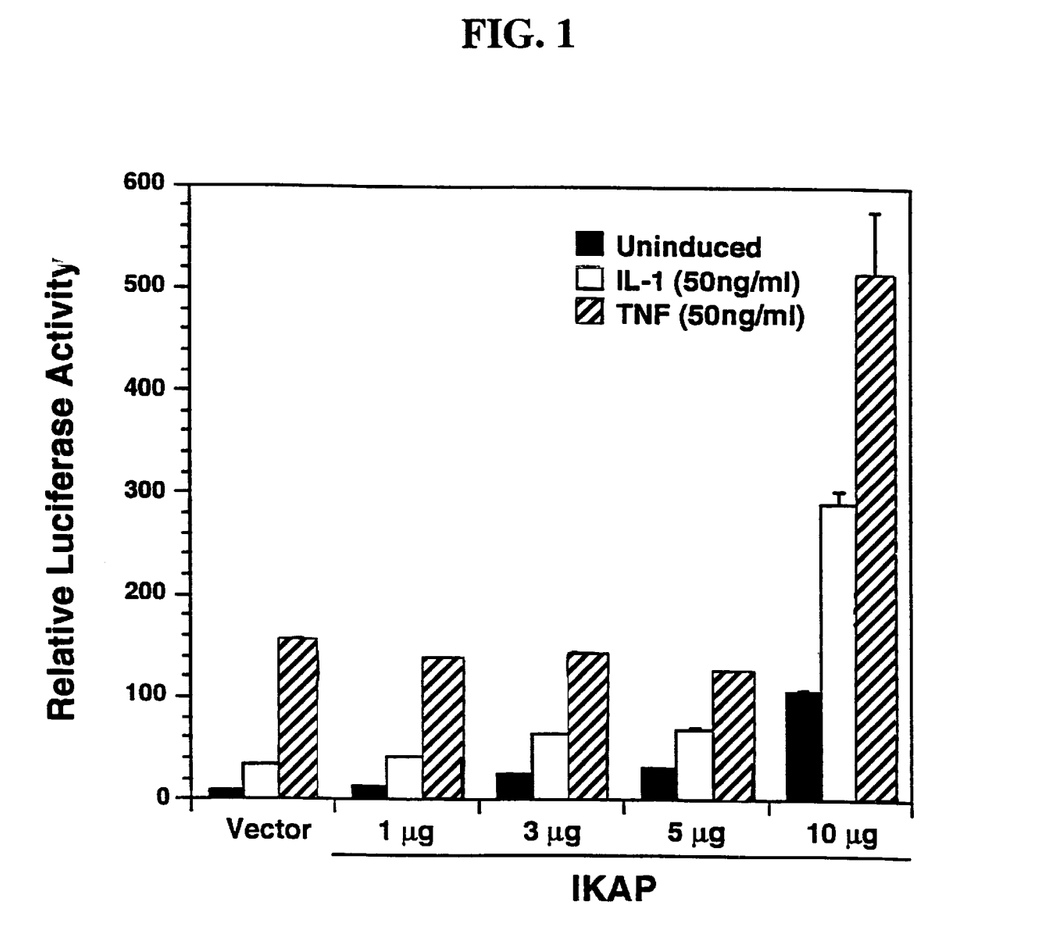
FIG. 1. IKAP polypeptides activate NFκB.

The nucleotide sequence of a natural cDNA encoding a human IKAP polypeptide is shown as SEQ ID NO:1, and the full conceptual translate is shown as SEQ ID NO:2. The IKAP polypeptides of the invention include one or more functional domains of SEQ ID NO:2, which domains comprise at least 8, preferably at least 16, more preferably at least 32, most preferably at least 64 contiguous residues of SEQ ID NO:2 and have human IKAP-specific amino acid sequence and activity. IKAP domain specific activities include NIK-binding or binding inhibitory activity, NFκB-binding or binding inhibitory activity and IKAP specific immunogenicity and/or antigenicity.

IKAP-specific activity or function may be determined by convenient in vitro, cell-based, or in vivo assays: e.g. in vitro binding assays, cell culture assays, in animals (e.g. gene therapy, transgenics, etc.), etc. Binding assays encompass any assay where the molecular interaction of an IKAP polypeptide with a binding target is evaluated. The binding target may be a natural intracellular binding target such as an IKAP binding target, a IKAP regulating protein or other regulator that directly modulates IKAP activity or its localization; or non-natural binding target such a specific immune protein such as an antibody, or an IKAP specific agent such as those identified in screening assays such as described below. IKAP-binding specificity may assayed by binding equilibrium constants (usually at least about $10^7 M^{-1}$, preferably at least about $10^8 M^{-1}$, more preferably at least about $10^9 M^{-1}$), by NFκB reporter expression, by the ability of the subject polypeptide to function as negative mutants in IKAP-expressing cells, to elicit IKAP specific antibody in a heterologous host (e.g a rodent or rabbit), etc.

For example, deletion mutagenesis is used to defined functional IKAP domains which activate NFκB expression or function as dominant/negative mutants in IKAP-mediated NFκB activation assays. See, e.g. Table 1.

TABLE 1

Exemplary IKAP deletion mutants defining IKAP functional domains.

| Mutant | Sequence | NFκB | Dom/Neg |
|--------|----------|------|---------|
| ΔN1 | SEQ ID NO:2, residues 42-1332 | + | − |
| ΔN2 | SEQ ID NO:2, residues 142-1332 | + | − |
| ΔN3 | SEQ ID NO:2, residues 242-1332 | + | − |
| ΔN4 | SEQ ID NO:2, residues 342-1332 | + | − |
| ΔN5 | SEQ ID NO:2, residues 442-1332 | + | − |
| ΔC1 | SEQ ID NO:2, residues 1-923 | − | + |
| ΔC2 | SEQ ID NO:2, residues 1-441 | − | |
| ΔC3 | SEQ ID NO:2, residues 1-241 | − | |
| ΔC4 | SEQ ID NO:2, residues 1-241 | − | |

In a particular embodiment, the subject domains provide IKAP-specific antigens and/or immunogens, especially when coupled to carrier proteins. For example, peptides corresponding to IKAP- and human IKAP-specific domains are covalently coupled to keyhole limpet antigen (KLH) and the conjugate is emulsified in Freunds complete adjuvant. Laboratory rabbits are immunized according to conventional protocol and bled. The presence of IKAP-specific antibodies is assayed by solid phase immunosorbant assays using immobilized IKAP polypeptides of SEQ ID NO:2, see, e.g. Table 2.

TABLE 2

Immunogenic IKAP polypeptides eliciting IKAP-specific rabbit polyclonal antibody: IKAP polypeptide-KLH conjugates immunized per protocol described above.

| IKAP Polypeptide Sequence | Immunogenicity |
|---------------------------|----------------|
| SEQ ID NO:2, residues 1-10 | +++ |
| SEQ ID NO:2, residues 29-41 | +++ |
| SEQ ID NO:2, residues 75-87 | +++ |
| SEQ ID NO:2, residues 92-109 | +++ |
| SEQ ID NO:2, residues 132-141 | +++ |
| SEQ ID NO:2, residues 192-205 | +++ |
| SEQ ID NO:2, residues 258-269 | +++ |
| SEQ ID NO:2, residues 295-311 | +++ |
| SEQ ID NO:2, residues 316-330 | +++ |
| SEQ ID NO:2, residues 373-382 | +++ |
| SEQ ID NO:2, residues 403-422 | +++ |
| SEQ ID NO:2, residues 474-485 | +++ |
| SEQ ID NO:2, residues 561-576 | +++ |
| SEQ ID NO:2, residues 683-697 | +++ |
| SEQ ID NO:2, residues 768-777 | +++ |
| SEQ ID NO:2, residues 798-813 | +++ |
| SEQ ID NO:2, residues 882-894 | +++ |
| SEQ ID NO:2, residues 934-946 | +++ |
| SEQ ID NO:2, residues 1054-1067 | +++ |
| SEQ ID NO:2, residues 1181-1192 | +++ |
| SEQ ID NO:2, residues 1273-1282 | +++ |
| SEQ ID NO:2, residues 1283-1294 | +++ |
| SEQ ID NO:2, residues 1295-1312 | +++ |
| SEQ ID NO:2, residues 1313-1332 | +++ |

The claimed IKAP polypeptides are isolated or pure: an "isolated" polypeptide is unaccompanied by at least some of the material with which it is associated in its natural state, preferably constituting at least about 0.5%, and more preferably at least about 5% by weight of the total polypeptide in a given sample and a pure polypeptide constitutes at least about 90%, and preferably at least about 99% by weight of the total polypeptide in a given sample. The IKAP polypeptides and polypeptide domains may be synthesized, produced by recombinant technology, or purified from mammalian, preferably human cells. A wide variety of molecular and biochemical methods are available for biochemical synthesis, molecular expression and purification of the subject compositions, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, NY) or that are otherwise known in the art.

The invention provides binding agents specific to IKAP polypeptides, preferably the claimed IKAP polypeptides, including substrates, agonists, antagonists, natural intracellular binding targets, etc., methods of identifying and making such agents, and their use in diagnosis, therapy and pharmaceutical development. For example, specific binding agents are useful in a variety of diagnostic and therapeutic applications, especially where disease or disease prognosis is associated with improper utilization of a pathway involving the subject proteins, e.g. NF-κB activation. Novel IKAP-specific binding agents include IKAP-specific receptors, such as somatically recombined polypeptide receptors like specific antibodies or T-cell antigen receptors (see, e.g Harlow and Lane (1988) Antibodies, A Laboratory Manual, Cold Spring Harbor Laboratory) and other natural intracellular binding agents identified with assays such as one-, two- and three-hybrid screens, non-natural intracellular binding agents identified in screens of chemical libraries such as described below, etc. Agents of particular interest modulate IKAP function, e.g. IKAP-dependent transcriptional activation.

Accordingly, the invention provides methods for modulating signal transduction involving NFκB in a cell comprising the step of modulating IKAP activity. The cell may reside in culture or in situ, i.e. within the natural host. For diagnostic uses, the inhibitors or other IKAP binding agents are frequently labeled, such as with fluorescent, radioactive, chemiluminescent, or other easily detectable molecules, either conjugated directly to the binding agent or conjugated to a probe specific for the binding agent. Exemplary inhibitors include nucleic acids encoding dominant/negative mutant forms of IKAP, as described above, etc.

The amino acid sequences of the disclosed IKAP polypeptides are used to back-translate IKAP polypeptide-encoding nucleic acids optimized for selected expression systems (Holler et al. (1993) Gene 136, 323-328; Martin et al. (1995) Gene 154, 150–166) or used to generate degenerate oligonucleotide primers and probes for use in the isolation of natural IKAP-encoding nucleic acid sequences ("GCG" software, Genetics Computer Group, Inc, Madison, Wis.). IKAP-encoding nucleic acids used in IKAP-expression vectors and incorporated into recombinant host cells, e.g. for expression and screening, transgenic animals, e.g. for functional studies such as the efficacy of candidate drugs for disease associated with IKAP-modulated cell function, etc.

The invention also provides nucleic acid hybridization probes and replication/amplification primers having a IKAP cDNA specific sequence comprising at least 12, preferably at least 24, more preferably at least 36 and most preferably at least contiguous 96 bases of a strand of SEQ ID NO:1 sufficient to specifically hybridize with a second nucleic acid comprising the complementary strand of SEQ ID NO:1. Demonstrating specific hybridization generally requires stringent conditions, for example, hybridizing in a buffer comprising 30% formamide in 5×SSPE (0.18 M NaCl, 0.01 M NaPO$_4$, pH7.7, 0.001 M EDTA) buffer at a temperature of 42° C. and remaining bound when subject to washing at 42° C. with 0.2×SSPE; preferably hybridizing in a buffer comprising 50% formamide in 5×SSPE buffer at a temperature of 42° C. and remaining bound when subject to washing at 42° C. with 0.2×SSPE buffer at 42° C.

TABLE 3

Exemplary IKAP nucleic acids which hybridize with a strand of SEQ ID NO:1 under Conditions I and/or II.

| IKAP Nucleic Acids | Hybridization |
|---|---|
| SEQ ID NO:1, nucleotides 1-47 | + |
| SEQ ID NO:1, nucleotides 58-99 | + |
| SEQ ID NO:1, nucleotides 95-138 | + |
| SEQ ID NO:1, nucleotides 181-220 | + |
| SEQ ID NO:1, nucleotides 261-299 | + |
| SEQ ID NO:1, nucleotides 274-315 | + |
| SEQ ID NO:1, nucleotides 351-389 | + |
| SEQ ID NO:1, nucleotides 450-593 | + |
| SEQ ID NO:1, nucleotides 524-546 | + |
| SEQ ID NO:1, nucleotides 561-608 | + |
| SEQ ID NO:1, nucleotides 689-727 | + |
| SEQ ID NO:1, nucleotides 808-837 | + |
| SEQ ID NO:1, nucleotides 938-1001 | + |
| SEQ ID NO:1, nucleotides 1205-1254 | + |
| SEQ ID NO:1, nucleotides 1855-1907 | + |
| SEQ ID NO:1, nucleotides 2910-2953 | + |
| SEQ ID NO:1, nucleotides 3967-3999 | + |

The subject nucleic acids are of synthetic/non-natural sequences and/or are isolated, i.e. unaccompanied by at least some of the material with which it is associated in its natural state, preferably constituting at least about 0.5%, preferably at least about 5% by weight of total nucleic acid present in a given fraction, and usually recombinant, meaning they comprise a non-natural sequence or a natural sequence joined to nucleotide(s) other than that which it is joined to on a natural chromosome. Recombinant nucleic acids comprising the nucleotide sequence of SEQ ID NO:1, or requisite fragments thereof, contain such sequence or fragment at a terminus, immediately flanked by (i.e. contiguous with) a sequence other than that which it is joined to on a natural chromosome, or flanked by a native flanking region fewer than 10 kb, preferably fewer than 2 kb, which is at a terminus or is immediately flanked by a sequence other than that which it is joined to on a natural chromosome. While the nucleic acids are usually RNA or DNA, it is often advantageous to use nucleic acids comprising other bases or nucleotide analogs to provide modified stability, etc.

The subject nucleic acids find a wide variety of applications including use as translatable transcripts, hybridization probes, PCR primers, diagnostic nucleic acids, etc.; use in detecting the presence of IKAP genes and gene transcripts and in detecting or amplifying nucleic acids encoding additional IKAP homologs and structural analogs. In diagnosis, IKAP hybridization probes find use in identifying wild-type and mutant IKAP alleles in clinical and laboratory samples. Mutant alleles are used to generate allele-specific oligonucleotide (ASO) probes for high-throughput clinical diagnoses. In therapy, therapeutic IKAP nucleic acids are used to modulate cellular expression or intracellular concentration or availability of active IKAP.

The invention provides efficient methods of identifying agents, compounds or lead compounds for agents active at the level of a IKAP modulatable cellular function. Generally, these screening methods involve assaying for compounds which modulate IKAP interaction with a natural IKAP binding target, such as NIK A wide variety of assays for binding agents are provided including labeled in vitro protein-protein binding assays, immunoassays, cell based assays, etc. The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development.

In vitro binding assays employ a mixture of components including an IKAP polypeptide, which may be part of a fusion product with another peptide or polypeptide, e.g. a tag for detection or anchoring, etc. The assay mixtures comprise a natural intracellular IKAP binding target. While native full-length binding targets may be used, it is frequently preferred to use portions (e.g. peptides) thereof so long as the portion provides binding affinity and avidity to the subject IKAP polypeptide conveniently measurable in the assay. The assay mixture also comprises a candidate pharmacological agent. Candidate agents encompass numerous chemical classes, though typically they are organic compounds; preferably small organic compounds and are obtained from a wide variety of sources including libraries of synthetic or natural compounds. A variety of other reagents may also be included in the mixture. These include reagents like salts, buffers, neutral proteins, e.g. albumin, detergents, protease inhibitors, nuclease inhibitors, antimicrobial agents, etc. may be used.

The resultant mixture is incubated under conditions whereby, but for the presence of the candidate pharmacological agent, the IKAP polypeptide specifically binds the cellular binding target, portion or analog with a reference binding affinity. The mixture components can be added in any order that provides for the requisite bindings and incubations may be performed at any temperature which facilitates optimal binding. Incubation periods are likewise selected for optimal binding but also minimized to facilitate rapid, high-throughput screening.

After incubation, the agent-biased binding between the IKAP polypeptide and one or more binding targets is detected by any convenient way. A difference in the binding affinity of the IKAP polypeptide to the target in the absence of the agent as compared with the binding affinity in the presence of the agent indicates that the agent modulates the binding of the IKAP polypeptide to the IKAP binding target. Analogously, in the cell-based assay also described below, a difference in IKAP-dependent transcriptional activation in the presence and absence of an agent indicates the agent modulates IKAP function. A difference, as used herein, is statistically significant and preferably represents at least a 50%, more preferably at least a 90% difference.

The following experimental section and examples are offered by way of illustration and not by way of limitation.

EXAMPLES

1. Protocol for Cell-based IKAP-NIK Interaction Assay

IKAP has been identified as a NIK-interacting protein by coprecipitation assay: 293 cells are transfected with mammalian expression vectors encoding Flag-tagged NIK and Myc-tagged IKAP respectively. After 48 hours, cells are collected, washed twice with phosphate-buffered saline and lysed for 30 min at 4° C. in 0.5 ml of lysis buffer (50 mM HEPES pH 7.6, 100 mM NaCl, 1% NP-40, 1 mM EDTA, 10% glycerol) containing phosphatase and protease inhibitors. Cellular debris is removed by centrifugation at 10,000×g for 10 min twice. The NaCl concentration of the cell lysates is increased to 250 mM. The cell lysates are incubated for 1 hour on ice with 1 μg of anti-Flag monoclonal antibody or control mouse IgGl antibody, and an additional hour at 4° C. with 15 μl of protein G-agarose beads.The beads are then collected, and washed four times with 1 ml of lysis buffer containing 250 mM NaCl. The bound proteins are eluted, fractionated by SDS-PAGE and analyzed by western blotting using anti-Myc or anti-Flag polyclonal antibodies. The immunoblot is developed with horseradish peroxidase-coupled goat anti-rabbit immunoglobin as secondary antibody and visualized using the Enhanced Chemoluminescence (ECL) Detection System.

2. Protocol for Cell-based NF-κB Reporter Assay

IKAP can trans-activate NF-κB reporter constructs when overexpressed in 293 cells or HeLa cells. 293 cells are transfected using the calcium phosphate precipitation method with a plasmid encoding a 6 NF-κB-luciferase reporter construct and various amounts of expression vector encoding IKAP. After 36–48 hours, cells are left untreated or treated with IL-1 (10–50 ng/ml) or TNF (50–100 ng) for 6 hours prior to harvest. Cells are lysed and luciferase activity measured using the luciferase assay kit (Promega). The luciferase activity in each transfection is normalized by co-transfecting a pRSV-β gal control vector.

3. Protocol for High Throughput in Vitro IKAP-NIK Binding Assay.

A. Reagents:

Neutralite Avidin: 20 μg/ml in PBS.

Blocking buffer: 5% BSA, 0.5% Tween 20 in PBS; 1 hour at room temperature.

Assay Buffer: 100 mM KCl, 20 mM HEPES pH 7.6, 1 mM $MgCl_2$, 1% glycerol, 0.5% NP-40, 50 mM β-mercaptoethanol, 1 mg/ml BSA, cocktail of protease inhibitors.

$^{33}$P IKAP polypeptide 10×stock: $10^{-8}$–$10^{-6}$M "cold" IKAP supplemented with 200,000–250,000 cpm of labeled IKAP (Beckman counter). Place in the 4° C. microfridge during screening.

Protease inhibitor cocktail (1000X): 10 mg Trypsin Inhibitor (BMB #109894), 10 mg Aprotinin (BMB # 236624), 25 mg Benzamidine (Sigma #B-6506), 25 mg Leupeptin (BMB #1017128), 10 mg APMSF (BMB #917575), and 2 mM $NaVO_3$ (Sigma #S-6508) in 10 ml of PBS.

NIK: $10^{-7}$–$10^{-5}$ M biotinylated NIK in PBS.

B. Preparation of Assay Plates:

Coat with 120 μl of stock N-Avidin per well overnight at 4° C.

Wash 2 times with 200 μl PBS.

Block with 150 μl of blocking buffer.

Wash 2 times with 200 μl PBS.

C. Assay:

Add 40 μl assay buffer/well.

Add 10 μl compound or extract.

Add 10 μl $^{33}$P-IKAP (20–25,000 cpm/0.1–10 pmoles/well=$10^{-9}$–$10^{-7}$ M final conc).

Shake at 25° C. for 15 minutes.

Incubate additional 45 minutes at 25° C.

Add 40 uM biotinylated NIK (0.1–10 pmoles/40 μl in assay buffer)

Incubate 1 hour at room temperature.

Stop the reaction by washing 4 times with 200 μM PBS.

Add 150 μM scintillation cocktail.

Count in Topcount.

D. Controls For All Assays (Located on Each Plate):

a. Non-specific binding b. Soluble (non-biotinylated NIK) at 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated polypeptide comprising SEQ ID NO:2 or a fragment thereof selected from the group consisting of: residues 1–10, 29–41, 75–87, 92–109, 132–141, 192–205, 258–269, 295–311, 316–330, 373–382, 403–422, 474–485, 561–576, 683–697, 768–777, 798–813, 1054–1067, 1181–1192, 1273–1282, 1283–1294, 1295–1312 and 1313–1332.

2. A polypeptide according to claim 1 comprising SEQ ID NO:2 residues 1–10.

3. A polypeptide according to claim 1 comprising SEQ ID NO:2 residues 29–41.

4. A polypeptide according to claim 1 comprising SEQ ID NO:2 residues 75–87.

5. A polypeptide according to claim 1 comprising SEQ ID NO:2 residues 92–109.

6. A polypeptide according to claim 1 comprising SEQ ID NO:2 residues 132–141.

7. A polypeptide according to claim 1 comprising SEQ ID NO:2 residues 192–205.

8. A polypeptide according to claim 1 comprising SEQ ID NO:2 residues 258–269.

9. A polypeptide according to claim 1 comprising SEQ ID NO:2 residues 295–311.

10. A polypeptide according to claim 1 comprising SEQ ID NO:2 residues 316–330.

11. A polypeptide according to claim 1 comprising SEQ ID NO:2 residues 373–382.

12. A polypeptide according to claim 1 comprising SEQ ID NO:2 residues 403–422.

13. A polypeptide according to claim 1 comprising SEQ ID NO:2 residues 474–485.

14. A polypeptide according to claim 1 comprising SEQ ID NO:2 residues 561–576.

15. A polypeptide according to claim 1 comprising SEQ ID NO:2 residues 683–697.

16. A polypeptide according to claim 1 comprising SEQ ID NO:2 residues 768–777.

17. A polypeptide according to claim 1 comprising SEQ ID NO:2 residues 798–813.

18. A polypeptide according to claim 1 comprising SEQ ID NO:2 residues 1054–1067.

19. A polypeptide according to claim 1 comprising SEQ ID NO:2 residues 1181–1192.

20. A polypeptide according to claim 1 comprising SEQ ID NO:2 residues 1273–1282.

21. A polypeptide according to claim 1 comprising SEQ ID NO:2 residues 1283–1294.

22. A polypeptide according to claim 1 comprising SEQ ID NO:2 residues 1295–1312.

23. A polypeptide according to claim 1 comprising SEQ ID NO:2 residues 1313–1332.

24. A polypeptide according to claim 1 comprising SEQ ID NO:2.

25. A method of screening for an agent which modulates the interaction of an IKAP polypeptide to a binding target, said method comprising the steps of:

incubating a mixture comprising:
        an isolated polypeptide according to claim 24,
        a binding target of said polypeptide, and
        a candidate agent;
    under conditions whereby, but for the presence of said agent, said polypeptide specifically binds said binding target at a reference affinity;
    detecting the binding affinity of said polypeptide to said binding target to determine an agent-biased affinity, wherein a difference between the agent-biased affinity and the reference affinity indicates that said agent modulates the binding of said polypeptide to said binding target.

26. A method according to claim 25, wherein the binding target is a NIK polypeptide.

* * * * *

```
                          SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
          (A) LENGTH: 3999 base pairs
          (B) TYPE: nucleic acid
          (C) STRANDEDNESS: double
          (D) TOPOLOGY: linear (ii) MOLECULE TYPE: cDNA (ix) FEATURE:
          (A) NAME/KEY: CDS
          (B) LOCATION: 1..3996

(xi) SEQUENCE DESCRIPTION: SEQ ID NO:1:

ATG CGA AAT CTG AAA TTA TTT CGG ACC CTG GAG TTC AGG GAT ATT CAA        48
Met Arg Asn Leu Lys Leu Phe Arg Thr Leu Glu Phe Arg Asp Ile Gln
 1               5                  10                  15

GGT CCA GGG AAT CCT CAG TGC TTC TCT CTC CGA ACT GAA CAG GGG ACG        96
Gly Pro Gly Asn Pro Gln Cys Phe Ser Leu Arg Thr Glu Gln Gly Thr
             20                  25                  30

GTG CTC ATT GGT TCA GAA CAT GGC CTG ATA GAA GTA GAC CCT GTC TCA       144
Val Leu Ile Gly Ser Glu His Gly Leu Ile Glu Val Asp Pro Val Ser
         35                  40                  45

AGA GAA GTG AAA AAT GAA GTT TCT TTG GTG GCA GAA GGC TTT CTT CCA       192
Arg Glu Val Lys Asn Glu Val Ser Leu Val Ala Glu Gly Phe Leu Pro
     50                  55                  60

GAG GAT GGA AGT GGC CGC ATT GTT GGT GTT CAG GAC TTG CTG GAT CAG       240
Glu Asp Gly Ser Gly Arg Ile Val Gly Val Gln Asp Leu Leu Asp Gln
 65                  70                  75                  80

GAG TCT GTG TGT GTG GCC ACA GCC TCT GGA GAC GTC ATA CTC TGC AGT       288
Glu Ser Val Cys Val Ala Thr Ala Ser Gly Asp Val Ile Leu Cys Ser
                 85                  90                  95

CTC AGC ACA CAA CAG CTG GAG TGT GTT GGG AGT GTA GCC AGT GGT ATC       336
Leu Ser Thr Gln Gln Leu Glu Cys Val Gly Ser Val Ala Ser Gly Ile
            100                 105                 110

TCT GTT ATG AGT TGG AGT CCT GAC CAA GAG CTG GTG CTT CTT GCC ACA       384
Ser Val Met Ser Trp Ser Pro Asp Gln Glu Leu Val Leu Leu Ala Thr
        115                 120                 125

GGT CAA CAG ACC CTG ATT ATG ATG ACA AAA GAT TTT GAG CCA ATC CTG       432
Gly Gln Gln Thr Leu Ile Met Met Thr Lys Asp Phe Glu Pro Ile Leu
    130                 135                 140

GAG CAG CAG ATC CAT CAG GAT GAT TTT GGT GAA AGC AAG TTT ATC ACT       480
Glu Gln Gln Ile His Gln Asp Asp Phe Gly Glu Ser Lys Phe Ile Thr
145                 150                 155                 160

GTT GGA TGG GGT AGG AAG GAG ACA CAG TTC CAT GGA TCA GAA GGC AGA       528
Val Gly Trp Gly Arg Lys Glu Thr Gln Phe His Gly Ser Glu Gly Arg
                165                 170                 175

CAA GCA GCT TTT CAG ATG CAA ATG CAT GAG TCT GCT TTG CCC TGG GAT       576
Gln Ala Ala Phe Gln Met Gln Met His Glu Ser Ala Leu Pro Trp Asp
            180                 185                 190

GAC CAT AGA CCA CAA GTT ACC TGG CGG GGG GAT GGA CAG TTT TTT GCT       624
```

-continued

```
                Asp His Arg Pro Gln Val Thr Trp Arg Gly Asp Gly Gln Phe Phe Ala
                        195                 200                 205

GTG AGT GTT GTT TGC CCA GAA ACA GGG GCT CGG AAG GTC AGA GTG TGG        672
Val Ser Val Val Cys Pro Glu Thr Gly Ala Arg Lys Val Arg Val Trp
    210                 215                 220

AAC CGA GAG TTT GCT TTG CAG TCA ACC AGT GAG CCT GTG GCA GGA CTG        720
Asn Arg Glu Phe Ala Leu Gln Ser Thr Ser Glu Pro Val Ala Gly Leu
225                 230                 235                 240

GGA CCA GCC CTG GCT TGG AAA CCC TCA GGC AGT TTG ATT GCA TCT ACA        768
Gly Pro Ala Leu Ala Trp Lys Pro Ser Gly Ser Leu Ile Ala Ser Thr
                245                 250                 255

CAA GAT AAA CCC AAC CAG CAG GAT ATT GTG TTT TTT GAG AAA AAT GGA        816
Gln Asp Lys Pro Asn Gln Gln Asp Ile Val Phe Phe Glu Lys Asn Gly
            260                 265                 270

CTC CTT CAT GGA CAC TTT ACA CTT CCC TTC CTT AAA GAT GAG GTT AAG        864
Leu Leu His Gly His Phe Thr Leu Pro Phe Leu Lys Asp Glu Val Lys
        275                 280                 285

GTA AAT GAC TTG CTC TGG AAT GCA GAT TCC TCT GTG CTT GCA GTC CGG        912
Val Asn Asp Leu Leu Trp Asn Ala Asp Ser Ser Val Leu Ala Val Arg
    290                 295                 300

CTG GAA GAC CTT CAG AGA GAA AAA AGC TCC ATT CCG AAA ACC TGT GTT        960
Leu Glu Asp Leu Gln Arg Glu Lys Ser Ser Ile Pro Lys Thr Cys Val
305                 310                 315                 320

CAG CTC TGG ACT GTT GGA AAC TAT CAC TGG TAT CTC AAG CAA AGT TTA       1008
Gln Leu Trp Thr Val Gly Asn Tyr His Trp Tyr Leu Lys Gln Ser Leu
                325                 330                 335

TCC TTC AGC ACC TGT GGG AAG AGC AAG ATT GTG TCT CTG ATG TGG GAC       1056
Ser Phe Ser Thr Cys Gly Lys Ser Lys Ile Val Ser Leu Met Trp Asp
                340                 345                 350

CCT GTG ACC CCA TAC CGG CTG CAT GTT CTC TGT CAG GGC TGG CAT TAC       1104
Pro Val Thr Pro Tyr Arg Leu His Val Leu Cys Gln Gly Trp His Tyr
            355                 360                 365

CTC GCC TAT GAT TGG CAC TGG ACG ACT GAC CGG AGC GTG GGA GAT AAT       1152
Leu Ala Tyr Asp Trp His Trp Thr Thr Asp Arg Ser Val Gly Asp Asn
        370                 375                 380

TCA AGT GAC TTG TCC AAT GTG GCT GTC ATT GAT GGA AAC AGG GTG TTG       1200
Ser Ser Asp Leu Ser Asn Val Ala Val Ile Asp Gly Asn Arg Val Leu
385                 390                 395                 400

GTG ACA GTC TTC CGG CAG ACT GTG GTT CCG CCT CCC ATG TGC ACC TAC       1248
Val Thr Val Phe Arg Gln Thr Val Val Pro Pro Pro Met Cys Thr Tyr
                405                 410                 415

CAA CTG CTG TTC CCA CAC CCT GTG AAT CAA GTC ACA TTC TTA GCA CAC       1296
Gln Leu Leu Phe Pro His Pro Val Asn Gln Val Thr Phe Leu Ala His
                420                 425                 430

CCT CAA AAG AGT AAT GAC CTT GCT GTT CTA GAT GCC AGT AAC CAG ATT       1344
Pro Gln Lys Ser Asn Asp Leu Ala Val Leu Asp Ala Ser Asn Gln Ile
            435                 440                 445

TCT GTT TAT AAA TGT GGT GAT TGT CCA AGT GCT GAC CCT ACA GTG AAA       1392
Ser Val Tyr Lys Cys Gly Asp Cys Pro Ser Ala Asp Pro Thr Val Lys
        450                 455                 460

CTG GGA GCT GTG GGT GGA AGT GGA TTT AAA GTT TGC CTT AGA ACT CCT       1440
Leu Gly Ala Val Gly Gly Ser Gly Phe Lys Val Cys Leu Arg Thr Pro
465                 470                 475                 480

CAT TTG GAA AAG AGA TAC AAA ATC CAG TTT GAG AAT AAT GAA GAT CAA       1488
His Leu Glu Lys Arg Tyr Lys Ile Gln Phe Glu Asn Asn Glu Asp Gln
                485                 490                 495

GAT GTA AAC CCG CTG AAA CTA GGC CTT CTC ACT TGG ATT GAA GAA GAC       1536
Asp Val Asn Pro Leu Lys Leu Gly Leu Leu Thr Trp Ile Glu Glu Asp
                500                 505                 510
```

```
GTC TTC CTG GCT GTA AGC CAC AGT GAG TTC AGC CCC CGG TCT GTC ATT      1584
Val Phe Leu Ala Val Ser His Ser Glu Phe Ser Pro Arg Ser Val Ile
            515                 520                 525

CAC CAT TTG ACT GCA GCT TCT TCT GAG ATG GAT GAA GAG CAT GGA CAG      1632
His His Leu Thr Ala Ala Ser Ser Glu Met Asp Glu Glu His Gly Gln
            530                 535                 540

CTC AAT GTC AGT TCA TCT GCA GCG GTG GAT GGG GTC ATA ATC AGT CTA      1680
Leu Asn Val Ser Ser Ser Ala Ala Val Asp Gly Val Ile Ile Ser Leu
545                 550                 555                 560

TGT TGC AAT TCC AAG ACC AAG TCA GTA GTA TTA CAG CTG GCT GAT GGC      1728
Cys Cys Asn Ser Lys Thr Lys Ser Val Val Leu Gln Leu Ala Asp Gly
                565                 570                 575

CAG ATA TTT AAG TAC CTT TGG GAG TCA CCT TCT CTG GCT ATT AAA CCA      1776
Gln Ile Phe Lys Tyr Leu Trp Glu Ser Pro Ser Leu Ala Ile Lys Pro
            580                 585                 590

TGG AAG AAC TCT GGT GGA TTT CCT GTT CGG TTT CCT TAT CCA TGC ACC      1824
Trp Lys Asn Ser Gly Gly Phe Pro Val Arg Phe Pro Tyr Pro Cys Thr
            595                 600                 605

CAG ACC GAA TTG GCC ATG ATT GGA GAA GAG GAA TGT GTC CTT GGT CTG      1872
Gln Thr Glu Leu Ala Met Ile Gly Glu Glu Glu Cys Val Leu Gly Leu
610                 615                 620

ACT GAC AGG TGT CGC TTT TTC ATC AAT GAC ATT GAG GTT GCG TCA AAT      1920
Thr Asp Arg Cys Arg Phe Phe Ile Asn Asp Ile Glu Val Ala Ser Asn
625                 630                 635                 640

ATC ACG TCA TTT GCA GTA TAT GAT GAG TTT TTA TTG TTG ACA ACC CAT      1968
Ile Thr Ser Phe Ala Val Tyr Asp Glu Phe Leu Leu Leu Thr Thr His
                645                 650                 655

TCC CAT ACC TGC CAG TGT TTT TGC CTG AGG GAT GCT TCA TTT AAA ACA      2016
Ser His Thr Cys Gln Cys Phe Cys Leu Arg Asp Ala Ser Phe Lys Thr
            660                 665                 670

TTA CAG GCC GGC CTG AGC AGC AAT CAT GTG TCC CAT GGG GAA GTT CTG      2064
Leu Gln Ala Gly Leu Ser Ser Asn His Val Ser His Gly Glu Val Leu
            675                 680                 685

CGG AAA GTG GAG AGG GGT TCA CGG ATT GTC ACT GTT GTG CCC CAG GAC      2112
Arg Lys Val Glu Arg Gly Ser Arg Ile Val Thr Val Val Pro Gln Asp
690                 695                 700

ACA AAG CTT GTA TTA CAG ATG CCA AGG GGA AAC TTA GAA GTT GTT CAT      2160
Thr Lys Leu Val Leu Gln Met Pro Arg Gly Asn Leu Glu Val Val His
705                 710                 715                 720

CAT CGA GCC CTG GTT TTA GCT CAG ATT CGG AAG TGG TTG GAC AAA CTT      2208
His Arg Ala Leu Val Leu Ala Gln Ile Arg Lys Trp Leu Asp Lys Leu
                725                 730                 735

ATG TTT AAA GAG GCA TTT GAA TGC ATG AGA AAG CTG AGA ATC AAT CTC      2256
Met Phe Lys Glu Ala Phe Glu Cys Met Arg Lys Leu Arg Ile Asn Leu
            740                 745                 750

AAT CCG ATT TAT GAT CAT AAC CCT AAG GTG TTT CTT GGA AAT GTG GAA      2304
Asn Pro Ile Tyr Asp His Asn Pro Lys Val Phe Leu Gly Asn Val Glu
            755                 760                 765

ACC TTC ATT AAA CAG ATA GAT TCT GTG AAT CAT ATT AAC TTG TTT TTT      2352
Thr Phe Ile Lys Gln Ile Asp Ser Val Asn His Ile Asn Leu Phe Phe
770                 775                 780

ACA GAA TTG AAA GAA GAA GAT GTC ACG AAG ACC ATG TAC CCT GCA CCA      2400
Thr Glu Leu Lys Glu Glu Asp Val Thr Lys Thr Met Tyr Pro Ala Pro
785                 790                 795                 800

GTT ACC AGC AGT GTC TAC CTG TCC AGG GAT CCT GAC GGG AAT AAA ATA      2448
Val Thr Ser Ser Val Tyr Leu Ser Arg Asp Pro Asp Gly Asn Lys Ile
                805                 810                 815

GAC CTT GTC TGC GAT GCT ATG AGA GCA GTC ATG GAG AGC ATA AAT CCT      2496
Asp Leu Val Cys Asp Ala Met Arg Ala Val Met Glu Ser Ile Asn Pro
            820                 825                 830
```

```
CAT AAA TAC TGC CTA TCC ATA CTT ACA TCT CAT GTA AAG AAG ACA ACC    2544
His Lys Tyr Cys Leu Ser Ile Leu Thr Ser His Val Lys Lys Thr Thr
        835                 840                 845

CCA GAA CTG GAA ATT GTA CTG CAA AAA GTA CAC GAG CTT CAA GGA AAT    2592
Pro Glu Leu Glu Ile Val Leu Gln Lys Val His Glu Leu Gln Gly Asn
    850                 855                 860

GCT CCC TCT GAT CCT GAT GCT GTG AGT GCT GAA GAG GCC TTG AAA TAT    2640
Ala Pro Ser Asp Pro Asp Ala Val Ser Ala Glu Glu Ala Leu Lys Tyr
865                 870                 875                 880

TTG CTG CAT CTG GTA GAT GTT AAT GAA TTA TAT GAT CAT TCT CTT GGC    2688
Leu Leu His Leu Val Asp Val Asn Glu Leu Tyr Asp His Ser Leu Gly
            885                 890                 895

ACC TAT GAC TTT GAT TTG GTC CTC ATG GTA GCT GAG AAG TCA CAG AAG    2736
Thr Tyr Asp Phe Asp Leu Val Leu Met Val Ala Glu Lys Ser Gln Lys
        900                 905                 910

GAT CCC AAA GAA TAT CTT CCA TTT CTT AAT ACA CTT AAG AAA ATG GAA    2784
Asp Pro Lys Glu Tyr Leu Pro Phe Leu Asn Thr Leu Lys Lys Met Glu
    915                 920                 925

ACT AAT TAT CAG CGG TTT ACT ATA GAC AAA TAC TTG AAA CGA TAT GAA    2832
Thr Asn Tyr Gln Arg Phe Thr Ile Asp Lys Tyr Leu Lys Arg Tyr Glu
    930                 935                 940

AAA GCC ATT GGC CAC CTC AGC AAA TGT GGA CCT GAG TAC TTC CCA GAA    2880
Lys Ala Ile Gly His Leu Ser Lys Cys Gly Pro Glu Tyr Phe Pro Glu
945                 950                 955                 960

TGC TTA AAC TTG ATA AAA GAT AAA AAC TTG TAT AAC GAA GCT CTG AAG    2928
Cys Leu Asn Leu Ile Lys Asp Lys Asn Leu Tyr Asn Glu Ala Leu Lys
            965                 970                 975

TTA TAT TCA CCA AGC TCA CAA CAG TAC CAG GAT ATC AGC ATT GCT TAT    2976
Leu Tyr Ser Pro Ser Ser Gln Gln Tyr Gln Asp Ile Ser Ile Ala Tyr
        980                 985                 990

GGG GAG CAC CTG ATG CAG GAG CAC ATG TAT GAG CCA GCG GGG CTC ATG    3024
Gly Glu His Leu Met Gln Glu His Met Tyr Glu Pro Ala Gly Leu Met
    995                 1000                1005

TTT GCC CGT TGC GGT GCC CAC GAG AAA GCT CTC TCA GCC TTT CTC ACA    3072
Phe Ala Arg Cys Gly Ala His Glu Lys Ala Leu Ser Ala Phe Leu Thr
    1010                1015                1020

TGT GGC AAC TGG AAG CAA GCC CTC TGT GTG GCA GCC CAG CTT AAC TTT    3120
Cys Gly Asn Trp Lys Gln Ala Leu Cys Val Ala Ala Gln Leu Asn Phe
1025                1030                1035                1040

ACC AAA GAC CAG CTG GTG GGC CTC GGC AGA ACT CTG GCA GGA AAG CTG    3168
Thr Lys Asp Gln Leu Val Gly Leu Gly Arg Thr Leu Ala Gly Lys Leu
            1045                1050                1055

GTT GAG CAG AGG AAG CAC ATT GAT GCG GCC ATG GTT TTG GAA GAG TGT    3216
Val Glu Gln Arg Lys His Ile Asp Ala Ala Met Val Leu Glu Glu Cys
        1060                1065                1070

GCC CAG GAT TAT GAA GAA GCT GTG CTC TTG CTG TTA GAA GGA GCT GCC    3264
Ala Gln Asp Tyr Glu Glu Ala Val Leu Leu Leu Leu Glu Gly Ala Ala
    1075                1080                1085

TGG GAA GAA GCT TTG AGG CTG GTA TAC AAA TAT AAC AGA CTG GAT ATT    3312
Trp Glu Glu Ala Leu Arg Leu Val Tyr Lys Tyr Asn Arg Leu Asp Ile
    1090                1095                1100

ATA GAA ACC AAC GTA AAG CCT TCC ATT TTA GAA GCC AGA AAA AAT TAT    3360
Ile Glu Thr Asn Val Lys Pro Ser Ile Leu Glu Ala Gln Lys Asn Tyr
1105                1110                1115                1120

ATG GCA TTT CTG GAC TCT CAG ACA GCC ACA TTC AGT CGC CAC AAG AAA    3408
Met Ala Phe Leu Asp Ser Gln Thr Ala Thr Phe Ser Arg His Lys Lys
            1125                1130                1135

CGT TTA TTG GTA GTT CGA GAG CTC AAG GAG CAA GCC CAG CAG GCA GGT    3456
Arg Leu Leu Val Val Arg Glu Leu Lys Glu Gln Ala Gln Gln Ala Gly
```

| | | | | | | | | | | | | | | |
|---|---|---|---|---|---|---|---|---|---|---|---|---|---|---|
| | | 1140 | | | | | 1145 | | | | | 1150 | | |
| CTG | GAT | GAT | GAG | GTA | CCC | CAC | GGG | CAA | GAG | TCA | GAC | CTC | TTC | TCT | GAA | 3504 |
| Leu | Asp | Asp | Glu | Val | Pro | His | Gly | Gln | Glu | Ser | Asp | Leu | Phe | Ser | Glu |
| | | 1155 | | | | | 1160 | | | | | 1165 | | |

| ACT | AGC | AGT | GTC | GTG | AGT | GGC | AGT | GAG | ATG | AGT | GGC | AAA | TAC | TCC | CAT | 3552 |
| Thr | Ser | Ser | Val | Val | Ser | Gly | Ser | Glu | Met | Ser | Gly | Lys | Tyr | Ser | His |
| | | 1170 | | | | | 1175 | | | | | 1180 | | |

| AGT | AAC | TCC | AGG | ATA | TCA | GCG | AGA | TCA | TCC | AAG | AAT | CGC | CGA | AAA | GCG | 3600 |
| Ser | Asn | Ser | Arg | Ile | Ser | Ala | Arg | Ser | Ser | Lys | Asn | Arg | Arg | Lys | Ala |
| 1185 | | | | | 1190 | | | | | 1195 | | | | | 1200 |

| GAG | CGG | AAG | AAG | CAC | AGC | CTC | AAA | GAA | GGC | AGT | CCG | CTG | GAG | GAC | CTG | 3648 |
| Glu | Arg | Lys | Lys | His | Ser | Leu | Lys | Glu | Gly | Ser | Pro | Leu | Glu | Asp | Leu |
| | | | | 1205 | | | | | 1210 | | | | | 1215 | |

| GCC | CTC | CTG | GAG | GCA | CTG | AGT | GAA | GTG | GTG | CAG | AAC | ACT | GAA | AAC | CTG | 3696 |
| Ala | Leu | Leu | Glu | Ala | Leu | Ser | Glu | Val | Val | Gln | Asn | Thr | Glu | Asn | Leu |
| | | | 1220 | | | | | 1225 | | | | | 1230 | | |

| AAA | GAT | GAA | GTA | TAC | CAT | ATT | TTA | AAG | GTA | CTC | TTT | CTC | TTT | GAG | TTT | 3744 |
| Lys | Asp | Glu | Val | Tyr | His | Ile | Leu | Lys | Val | Leu | Phe | Leu | Phe | Glu | Phe |
| | | | 1235 | | | | | 1240 | | | | | 1245 | | |

| GAT | GAA | CAA | GGA | AGG | GAA | TTA | CAG | AAG | GCC | TTT | GAA | GAT | ACG | CTG | CAG | 3792 |
| Asp | Glu | Gln | Gly | Arg | Glu | Leu | Gln | Lys | Ala | Phe | Glu | Asp | Thr | Leu | Gln |
| | | 1250 | | | | | 1255 | | | | | 1260 | | | |

| TTG | ATG | GAA | AGG | TCA | CTT | CCA | GAA | ATT | TGG | ACT | CTT | ACT | TAC | CAG | CAG | 3840 |
| Leu | Met | Glu | Arg | Ser | Leu | Pro | Glu | Ile | Trp | Thr | Leu | Thr | Tyr | Gln | Gln |
| 1265 | | | | | 1270 | | | | | 1275 | | | | | 1280 |

| AAT | TCA | GCT | ACC | CCG | GTT | CTA | GGT | CCC | AAT | TCT | ACT | GCA | AAT | AGT | ATC | 3888 |
| Asn | Ser | Ala | Thr | Pro | Val | Leu | Gly | Pro | Asn | Ser | Thr | Ala | Asn | Ser | Ile |
| | | | | 1285 | | | | | 1290 | | | | | 1295 | |

| ATG | GCA | TCT | TAT | CAG | CAA | CAG | AAG | ACT | TCG | GTT | CCT | GTT | CTT | GAT | GCT | 3936 |
| Met | Ala | Ser | Tyr | Gln | Gln | Gln | Lys | Thr | Ser | Val | Pro | Val | Leu | Asp | Ala |
| | | | 1300 | | | | | 1305 | | | | | 1310 | | |

| GAG | CTT | TTT | ATA | CCA | CCA | AAG | ATC | AAC | AGA | AGA | ACC | CAG | TGG | AAG | CTG | 3984 |
| Glu | Leu | Phe | Ile | Pro | Pro | Lys | Ile | Asn | Arg | Arg | Thr | Gln | Trp | Lys | Leu |
| | | | 1315 | | | | | 1320 | | | | | 1325 | | |

| AGC | CTG | CTA | GAC | TGA | | | | | | | | | | | | 3999 |
| Ser | Leu | Leu | Asp | | | | | | | | | | | | |
| | | 1330 | | | | | | | | | | | | | |

(2) INFORMATION FOR SEQ ID NO:2:

(i) SEQUENCE CHARACTERISTICS:
        (A) LENGTH: 1332 amino acids
        (B) TYPE: amino acid
        (D) TOPOLOGY: linear     (ii) MOLECULE TYPE: protein     (xi) SEQUENCE DESCRIPTION: SEQ ID NO:2:

| Met | Arg | Asn | Leu | Lys | Leu | Phe | Arg | Thr | Leu | Glu | Phe | Arg | Asp | Ile | Gln |
|---|---|---|---|---|---|---|---|---|---|---|---|---|---|---|---|
| 1 | | | | 5 | | | | | 10 | | | | | 15 | |

| Gly | Pro | Gly | Asn | Pro | Gln | Cys | Phe | Ser | Leu | Arg | Thr | Glu | Gln | Gly | Thr |
| | | | 20 | | | | | 25 | | | | | 30 | | |

| Val | Leu | Ile | Gly | Ser | Glu | His | Gly | Leu | Ile | Glu | Val | Asp | Pro | Val | Ser |
| | | 35 | | | | | 40 | | | | | 45 | | | |

| Arg | Glu | Val | Lys | Asn | Glu | Val | Ser | Leu | Val | Ala | Glu | Gly | Phe | Leu | Pro |
| | 50 | | | | | 55 | | | | | 60 | | | | |

| Glu | Asp | Gly | Ser | Gly | Arg | Ile | Val | Gly | Val | Gln | Asp | Leu | Leu | Asp | Gln |
| 65 | | | | | 70 | | | | | 75 | | | | | 80 |

| Glu | Ser | Val | Cys | Val | Ala | Thr | Ala | Ser | Gly | Asp | Val | Ile | Leu | Cys | Ser |
| | | | | 85 | | | | | 90 | | | | | 95 | |

-continued

```
Leu Ser Thr Gln Gln Leu Glu Cys Val Gly Ser Val Ala Ser Gly Ile
            100                 105                 110
Ser Val Met Ser Trp Ser Pro Asp Gln Glu Leu Val Leu Leu Ala Thr
        115                 120                 125
Gly Gln Gln Thr Leu Ile Met Met Thr Lys Asp Phe Glu Pro Ile Leu
    130                 135                 140
Glu Gln Gln Ile His Gln Asp Asp Phe Gly Glu Ser Lys Phe Ile Thr
145                 150                 155                 160
Val Gly Trp Gly Arg Lys Glu Thr Gln Phe His Gly Ser Glu Gly Arg
                165                 170                 175
Gln Ala Ala Phe Gln Met Gln Met His Glu Ser Ala Leu Pro Trp Asp
            180                 185                 190
Asp His Arg Pro Gln Val Thr Trp Arg Gly Asp Gly Gln Phe Phe Ala
        195                 200                 205
Val Ser Val Val Cys Pro Glu Thr Gly Ala Arg Lys Val Arg Val Trp
    210                 215                 220
Asn Arg Glu Phe Ala Leu Gln Ser Thr Ser Glu Pro Val Ala Gly Leu
225                 230                 235                 240
Gly Pro Ala Leu Ala Trp Lys Pro Ser Gly Ser Leu Ile Ala Ser Thr
                245                 250                 255
Gln Asp Lys Pro Asn Gln Gln Asp Ile Val Phe Phe Glu Lys Asn Gly
            260                 265                 270
Leu Leu His Gly His Phe Thr Leu Pro Phe Leu Lys Asp Glu Val Lys
        275                 280                 285
Val Asn Asp Leu Leu Trp Asn Ala Asp Ser Ser Val Leu Ala Val Arg
    290                 295                 300
Leu Glu Asp Leu Gln Arg Glu Lys Ser Ser Ile Pro Lys Thr Cys Val
305                 310                 315                 320
Gln Leu Trp Thr Val Gly Asn Tyr His Trp Tyr Leu Lys Gln Ser Leu
                325                 330                 335
Ser Phe Ser Thr Cys Gly Lys Ser Lys Ile Val Ser Leu Met Trp Asp
            340                 345                 350
Pro Val Thr Pro Tyr Arg Leu His Val Leu Cys Gln Gly Trp His Tyr
        355                 360                 365
Leu Ala Tyr Asp Trp His Trp Thr Thr Asp Arg Ser Val Gly Asp Asn
    370                 375                 380
Ser Ser Asp Leu Ser Asn Val Ala Val Ile Asp Gly Asn Arg Val Leu
385                 390                 395                 400
Val Thr Val Phe Arg Gln Thr Val Val Pro Pro Pro Met Cys Thr Tyr
                405                 410                 415
Gln Leu Leu Phe Pro His Pro Val Asn Gln Val Thr Phe Leu Ala His
            420                 425                 430
Pro Gln Lys Ser Asn Asp Leu Ala Val Leu Asp Ala Ser Asn Gln Ile
        435                 440                 445
Ser Val Tyr Lys Cys Gly Asp Cys Pro Ser Ala Asp Pro Thr Val Lys
    450                 455                 460
Leu Gly Ala Val Gly Gly Ser Gly Phe Lys Val Cys Leu Arg Thr Pro
465                 470                 475                 480
His Leu Glu Lys Arg Tyr Lys Ile Gln Phe Glu Asn Asn Glu Asp Gln
                485                 490                 495
Asp Val Asn Pro Leu Lys Leu Gly Leu Leu Thr Trp Ile Glu Glu Asp
            500                 505                 510
```

-continued

```
Val Phe Leu Ala Val Ser His Ser Glu Phe Ser Pro Arg Ser Val Ile
        515                 520                 525

His His Leu Thr Ala Ala Ser Ser Glu Met Asp Glu His Gly Gln
        530                 535                 540

Leu Asn Val Ser Ser Ser Ala Ala Val Asp Gly Val Ile Ile Ser Leu
545                 550                 555                 560

Cys Cys Asn Ser Lys Thr Lys Ser Val Val Leu Gln Leu Ala Asp Gly
                565                 570                 575

Gln Ile Phe Lys Tyr Leu Trp Glu Ser Pro Ser Leu Ala Ile Lys Pro
            580                 585                 590

Trp Lys Asn Ser Gly Gly Phe Pro Val Arg Phe Pro Tyr Pro Cys Thr
            595                 600                 605

Gln Thr Glu Leu Ala Met Ile Gly Glu Glu Glu Cys Val Leu Gly Leu
            610                 615                 620

Thr Asp Arg Cys Arg Phe Phe Ile Asn Asp Ile Glu Val Ala Ser Asn
625                 630                 635                 640

Ile Thr Ser Phe Ala Val Tyr Asp Glu Phe Leu Leu Leu Thr Thr His
                645                 650                 655

Ser His Thr Cys Gln Cys Phe Cys Leu Arg Asp Ala Ser Phe Lys Thr
            660                 665                 670

Leu Gln Ala Gly Leu Ser Ser Asn His Val Ser His Gly Glu Val Leu
            675                 680                 685

Arg Lys Val Glu Arg Gly Ser Arg Ile Val Thr Val Pro Gln Asp
690                 695                 700

Thr Lys Leu Val Leu Gln Met Pro Arg Gly Asn Leu Glu Val Val His
705                 710                 715                 720

His Arg Ala Leu Val Leu Ala Gln Ile Arg Lys Trp Leu Asp Lys Leu
                725                 730                 735

Met Phe Lys Glu Ala Phe Glu Cys Met Arg Lys Leu Arg Ile Asn Leu
            740                 745                 750

Asn Pro Ile Tyr Asp His Asn Pro Lys Val Phe Leu Gly Asn Val Glu
            755                 760                 765

Thr Phe Ile Lys Gln Ile Asp Ser Val Asn His Ile Asn Leu Phe Phe
770                 775                 780

Thr Glu Leu Lys Glu Glu Asp Val Thr Lys Thr Met Tyr Pro Ala Pro
785                 790                 795                 800

Val Thr Ser Ser Val Tyr Leu Ser Arg Asp Pro Asp Gly Asn Lys Ile
                805                 810                 815

Asp Leu Val Cys Asp Ala Met Arg Ala Val Met Glu Ser Ile Asn Pro
            820                 825                 830

His Lys Tyr Cys Leu Ser Ile Leu Thr Ser His Val Lys Lys Thr Thr
            835                 840                 845

Pro Glu Leu Glu Ile Val Leu Gln Lys Val His Glu Leu Gln Gly Asn
850                 855                 860

Ala Pro Ser Asp Pro Asp Ala Val Ser Ala Glu Glu Ala Leu Lys Tyr
865                 870                 875                 880

Leu Leu His Leu Val Asp Val Asn Glu Leu Tyr Asp His Ser Leu Gly
                885                 890                 895

Thr Tyr Asp Phe Asp Leu Val Leu Met Val Ala Glu Lys Ser Gln Lys
            900                 905                 910

Asp Pro Lys Glu Tyr Leu Pro Phe Leu Asn Thr Leu Lys Lys Met Glu
            915                 920                 925

Thr Asn Tyr Gln Arg Phe Thr Ile Asp Lys Tyr Leu Lys Arg Tyr Glu
```

-continued

```
               930             935             940
Lys Ala Ile Gly His Leu Ser Lys Cys Gly Pro Glu Tyr Phe Pro Glu
945             950             955             960

Cys Leu Asn Leu Ile Lys Asp Lys Asn Leu Tyr Asn Glu Ala Leu Lys
                965             970             975

Leu Tyr Ser Pro Ser Ser Gln Gln Tyr Gln Asp Ile Ser Ile Ala Tyr
            980             985             990

Gly Glu His Leu Met Gln Glu His Met Tyr Glu Pro Ala Gly Leu Met
            995             1000            1005

Phe Ala Arg Cys Gly Ala His Glu Lys Ala Leu Ser Ala Phe Leu Thr
        1010            1015            1020

Cys Gly Asn Trp Lys Gln Ala Leu Cys Val Ala Ala Gln Leu Asn Phe
1025            1030            1035            1040

Thr Lys Asp Gln Leu Val Gly Leu Gly Arg Thr Leu Ala Gly Lys Leu
            1045            1050            1055

Val Glu Gln Arg Lys His Ile Asp Ala Ala Met Val Leu Glu Glu Cys
            1060            1065            1070

Ala Gln Asp Tyr Glu Glu Ala Val Leu Leu Leu Glu Gly Ala Ala
        1075            1080            1085

Trp Glu Glu Ala Leu Arg Leu Val Tyr Lys Tyr Asn Arg Leu Asp Ile
        1090            1095            1100

Ile Glu Thr Asn Val Lys Pro Ser Ile Leu Glu Ala Gln Lys Asn Tyr
1105            1110            1115            1120

Met Ala Phe Leu Asp Ser Gln Thr Ala Thr Phe Ser Arg His Lys Lys
            1125            1130            1135

Arg Leu Leu Val Val Arg Glu Leu Lys Glu Gln Ala Gln Ala Gly
            1140            1145            1150

Leu Asp Asp Glu Val Pro His Gly Gln Glu Ser Asp Leu Phe Ser Glu
            1155            1160            1165

Thr Ser Ser Val Val Ser Gly Ser Glu Met Ser Gly Lys Tyr Ser His
            1170            1175            1180

Ser Asn Ser Arg Ile Ser Ala Arg Ser Lys Asn Arg Arg Lys Ala
1185            1190            1195            1200

Glu Arg Lys Lys His Ser Leu Lys Glu Gly Ser Pro Leu Glu Asp Leu
            1205            1210            1215

Ala Leu Leu Glu Ala Leu Ser Glu Val Val Gln Asn Thr Glu Asn Leu
            1220            1225            1230

Lys Asp Glu Val Tyr His Ile Leu Lys Val Leu Phe Leu Phe Glu Phe
            1235            1240            1245

Asp Glu Gln Gly Arg Glu Leu Gln Lys Ala Phe Glu Asp Thr Leu Gln
            1250            1255            1260

Leu Met Glu Arg Ser Leu Pro Glu Ile Trp Thr Leu Thr Tyr Gln Gln
1265            1270            1275            1280

Asn Ser Ala Thr Pro Val Leu Gly Pro Asn Ser Thr Ala Asn Ser Ile
            1285            1290            1295

Met Ala Ser Tyr Gln Gln Lys Thr Ser Val Pro Val Leu Asp Ala
            1300            1305            1310

Glu Leu Phe Ile Pro Pro Lys Ile Asn Arg Arg Thr Gln Trp Lys Leu
            1315            1320            1325

Ser Leu Leu Asp
    1330
```